US010189969B2

(12) United States Patent
Boday et al.

(10) Patent No.: US 10,189,969 B2
(45) Date of Patent: Jan. 29, 2019

(54) SILICA-BASED ORGANOGELS VIA HEXAHYDROTRIAZINE-BASED REACTIONS

(71) Applicant: International Business Machines Corporation, Armonk, NY (US)

(72) Inventors: Dylan J. Boday, Tucson, AZ (US); Jeannette M. Garcia, San Leandro, CA (US); James L. Hedrick, Pleasanton, CA (US); Jason T. Wertz, Pleasant Valley, NY (US); Rudy J. Wojtecki, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 64 days.

(21) Appl. No.: 15/482,369

(22) Filed: Apr. 7, 2017

(65) Prior Publication Data

US 2018/0291173 A1    Oct. 11, 2018

(51) Int. Cl.
*C08J 9/28* (2006.01)
*C08G 101/00* (2006.01)

(52) U.S. Cl.
CPC ........ *C08J 9/28* (2013.01); *C08G 2101/0091* (2013.01); *C08J 2205/026* (2013.01); *C08J 2383/08* (2013.01)

(58) Field of Classification Search
CPC .................. C08J 2205/026; C08G 2101/0091
See application file for complete search history.

(56) References Cited

U.S. PATENT DOCUMENTS

| | | | |
|---|---|---|---|
| 7,071,287 B2 | 7/2006 | Rhine et al. | |
| 8,679,808 B2 | 3/2014 | Chen-Yang et al. | |
| 2012/0152846 A1 | 6/2012 | Leventis et al. | |
| 2012/0220679 A1* | 8/2012 | Fricke | C08G 18/7664 521/163 |
| 2013/0287661 A1* | 10/2013 | Begag | B01J 20/3085 423/228 |
| 2015/0176748 A1 | 6/2015 | Ikoma et al. | |
| 2016/0046495 A1 | 2/2016 | Xiang | |
| 2016/0090463 A1 | 3/2016 | Fricke et al. | |
| 2016/0115368 A1 | 4/2016 | Sadana et al. | |
| 2016/0272777 A1 | 9/2016 | Lee et al. | |

(Continued)

FOREIGN PATENT DOCUMENTS

WO        9425149 A1    11/1994

OTHER PUBLICATIONS

Husing, N.; Schubert, U. "Aerogels—Airy Materials: Chemistry, Structure, and Properties" Angew. Chem. Int. Ed. 1998, 37, 22 ± 45 (Year: 1998).*

(Continued)

*Primary Examiner* — Michael M Dollinger
*Assistant Examiner* — Christina H Wales
(74) *Attorney, Agent, or Firm* — Patterson + Sheridan, LLP

(57) ABSTRACT

Silica-based organogels, including aerogels, incorporating hexahydrotriazine and/or hemiaminal species are described. These organo-silica gel materials can have applications as insulating materials. In a particular example, an aerogel includes silica groups and a hexahydrotriazine moiety with at least one nitrogen atom that is covalently linked to a silica group. Methods of making such silica-based organogels are also described.

15 Claims, 6 Drawing Sheets

(56) References Cited

U.S. PATENT DOCUMENTS

2016/0289387 A1 10/2016 Wang et al.
2017/0114249 A1* 4/2017 Boday ................ C09D 201/025

OTHER PUBLICATIONS

Ciriminnia, et al. "Closing the Organosilicon Synthetic Cycle: Efficient Heterogeneous Hydrosilylation of Alkenes over SiliaCat Pt(0)", ACS Substainable Chemistry and Engineering, American Chemical Society, 2013, 5 pp.

Calas, et al., "Mechanical Strength Evolution from Aerogels to Silica Glass", Journal of Porous Materials, vol. 4, 1997, pp. 211-217.

Boday, et al. "Strong, Low-Density Nanocomposites by Chemical Vapor Deposition and Polymerization of Cyanoacrylates on Aminated Silica Aerogels" Applied Materials and Interfaces, vol. 1, No. 7, 2009, pp. 1364-1369.

* cited by examiner

SILICA-BASED ORGANOGELS VIA HEXAHYDROTRIAZINE-BASED REACTIONS

BACKGROUND

Materials and methods described herein relate to organogels and methods of making organogels. More particularly, silica-based organogels incorporating hexahydrotriazine-based moieties are described.

Aerogels are generally lightweight materials comprising a substantial amount of void (may be air or gas-filled) space. Aerogels are generally formed by the removal of a liquid component from an organogel, which is a gelled resin-type material. In general, aerogels result from supercritical drying of sol-gel polymerized materials. Some aerogels are known to be silica-based, carbon-based, or metal oxide-based. Some aerogels are potentially useful in applications such as thermal insulation and acoustic insulation.

SUMMARY

In one embodiment, an aerogel comprises a plurality of silica groups and a hexahydrotriazine moiety having at least one nitrogen atom that is covalently linked to at least one silica group in the plurality of silica groups. In some examples, the silica groups can be nanoparticles of silica (silicon dioxide).

Another embodiment described herein provides an insulating material comprising an organo-silica gel including a plurality of silica groups and a hexahydrotriazine group having at least one nitrogen atom covalently linked to at least one silica group in the plurality of silica groups. In some examples, the organo-silica gel can be an aerogel.

Another embodiment described herein provides a method comprising forming a reaction mixture including aniline silane material, a formaldehyde, and a solvent; forming a silica-based organogel from the reaction mixture; and drying the silica-based organogel. In some examples, after drying, the silica-based organogel can be an aerogel.

DETAILED DESCRIPTION

Figure 1A:
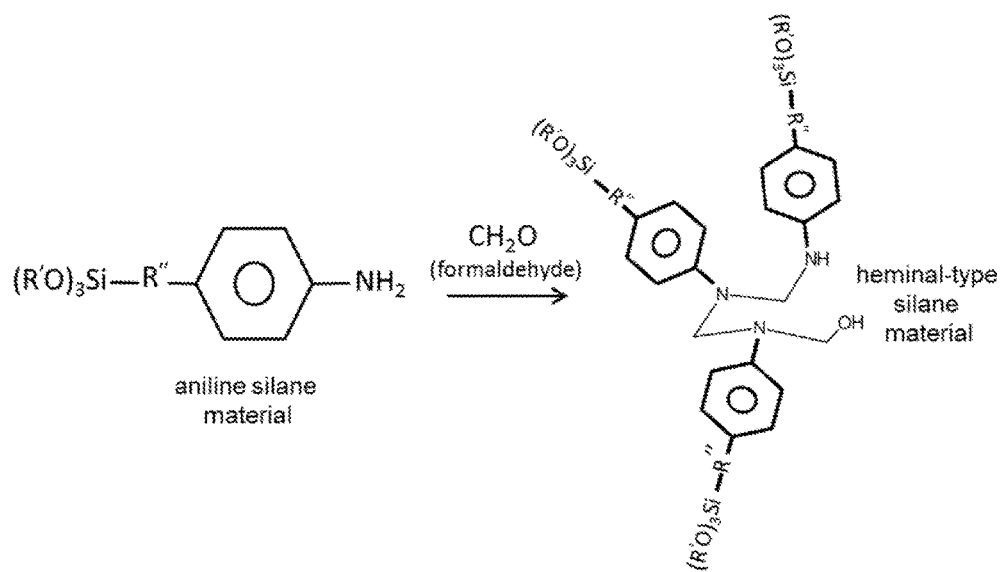
FIG. 1A depicts aspects of forming alkoxysilane functionalized hemiaminal material.

FIG. 1A depicts aspects of forming an alkoxysilane-functionalized hemiaminal material. An aniline silane material is reacted with formaldehyde to form an alkoxysilane-functionalized hemiaminal material. The resulting alkoxysilane-functionalized hemiaminal compound may be referred to as a hemiaminal-type silane material.

The aniline silane material comprises a primary amine group attached (covalently linked) to an aromatic ring group, which is depicted in FIG. 1A as a benzene ring for simplicity, but as described below may incorporate a more complex aromatic ring group. The aromatic ring group is further functionalized with an alkoxysilane group $(R'O)_3Si$— that is attached (covalently linked) to the aromatic ring group via a R'' group. In this context, each instance of R' may independently be one of a hydrogen (H) atom or an alkyl group including at least one carbon atom.

In some examples, R' can be a methyl group ($-CH_3$), an ethyl group ($-CH_2CH_3$), a propyl group ($-CH_2CH_2CH_3$), or, more generally, a linear alkyl group ($-(CH_2)_nCH_3$), where n is 0-10. In other examples, R' can be a branched alkyl group such as an isopropyl group ($-CH(CH_3)_2$) or a tert-butyl group ($-C(CH_3)_3$).

The R'' group may be a linking group, such as an alkyl linking (alkanediyl) group including at least one carbon. For example, R'' may be a methylene group ($-CH_2-$) or an ethanediyl group ($-CH_2CH_2-$). Furthermore, while the R'' group is depicted at the para position (relative to the amine group) on the ring, the R'' group could instead be at the meta position on the ring. In a particular example, R'' may be in the para position, R'' may be ethanediyl group, and R' in each of the three instances in alkoxysilane group may be an ethyl group.

At temperatures of about 50° C., the aniline silane material reacts with formaldehyde to form a substituted hemiaminal. This reaction can be carried out in a dipolar aprotic solvent, such as N-methyl-2-pyrrolidone (NMP), dimethylsulfoxide (DMSO), N,N-dimethylformamide (DMF), N,N-dimethylacetamide (DMA), propylene carbonate (PC), and/or propylene glycol methyl ether acetate (PGMEA). In some examples, the solvent may be omitted from the reaction mixture. The formaldehyde may be provided to the reaction mixture as paraformaldehyde.

Figure 1B:
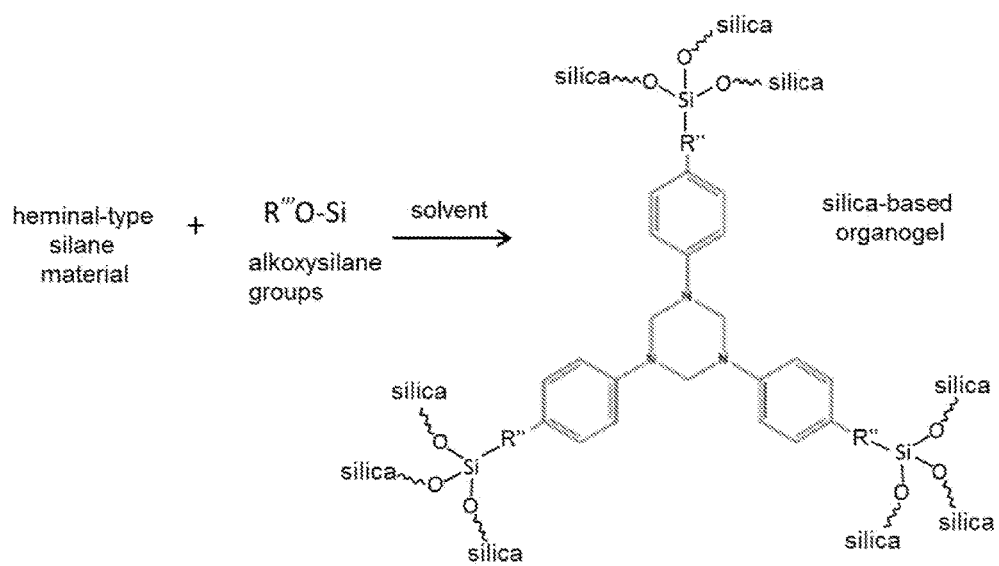
FIG. 1B depicts aspects of forming a silica-based organogel material incorporating hexahydrotriazine moieties.

Next, as depicted in FIG. 1B, the hemiaminal-type silane material (produced in FIG. 1A) can be reacted with an additional material including alkoxysilane groups (R'''OSi), where R''' includes at least one carbon atom. For example, the additional material may be tetramethyl orthosilicate, tetraethyl orthosilicate (referred to as "TEOS"), tetrapropyl orthosilicate, or other alkoxides of silicon.

The reaction is preferably carried out under dilute conditions to prevent the resulting gel material from becoming intractable. The solvent may be the same solvent described above in conjunction with FIG. 1A, but is not required to be. Furthermore, it is not necessary to isolate the hemiaminal-type silane material before reaction with the additional material including the alkoxysilane groups (R'''OSi). That is, the reactions in FIG. 1A and FIG. 1B may be carried out simultaneously within the same reaction vessel rather than serially.

The silica-based organogel product depicted in FIG. 1B includes hexahydrotriazine (HT) moieties, but this structure assumes that a subsequent heating process to a temperature above 50° C. is carried out to cause the conversion of the hemiaminal moiety into the HT moiety via elimination of a water molecule. Before such a heating process, the silica-based organogel may comprise hemiaminal moieties instead of the HT moieties depicted. FIG. 1B depicts silica groups (which are moieties incorporating one or more $SiO_2$ units) covalently linked to the hexahydrotriazine group.

The solvent used in the reaction of FIG. 1B may be any of the solvents described herein, or the solvent may be one or more excess precursors described above. The solvent generally maintains separation of polymer chains in the mixture to preserve the gel properties. The reaction of FIG. 1B may be performed at temperatures of 50° C. to 200° C.

The molar ratio of the hemiaminal-type silane material to the additional material including alkoxysilane groups (R'''OSi) in the reaction mixture may be varied from approximately 100% hemiaminal-type silane material to approximately 1% hemiaminal-type silane material according to the desired physical properties of the final product as well as the number of alkoxysilane groups per unit on the added material.

The silica-based organogel can then be dried to remove solvent. In some embodiments, the drying process may produce an aerogel. In other embodiments, depending on the drying process selection and/or processing conditions, a dry organogel, an aerogel precursor, a soft aerogel, or a hardened aerogel may be produced from the silica-based organogel material produced in FIG. 1B.

Figure 2:
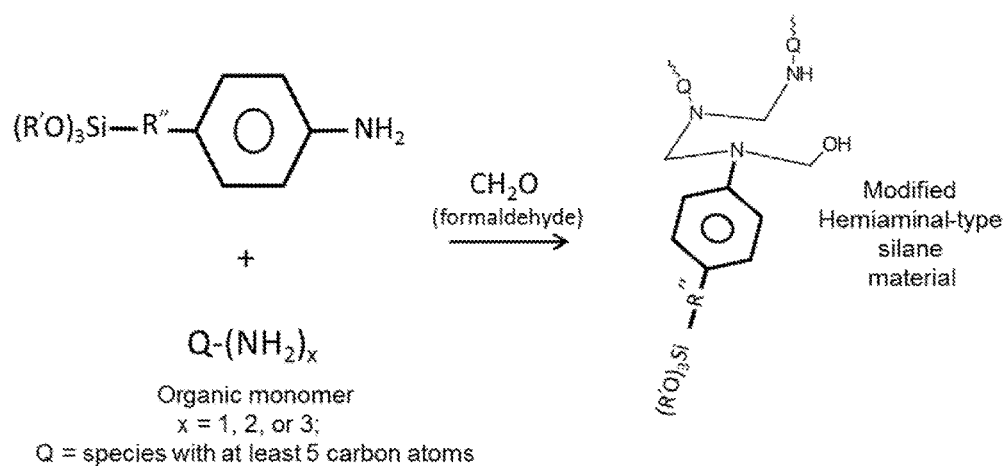
FIG. 2 depicts aspects of forming a modified precursor material of a silica-based organogel material.

FIG. 2 depicts another reaction scheme in which an additional monomer (or monomers) including at least one primary amine may be included in the reaction mixture along with the aniline silane material. Here, the aniline silane material is as was described above in conjunction with FIG. 1A. The other monomer has the general structure Q-(NH$_2$)$_x$, where Q is an organic species with at least 5 carbon atoms, and x is 1, 2, or 3 so Q is a monovalent, divalent, or trivalent radical.

The modified hemiaminal-type silane material formed in FIG. 2 can be reacted with a material including the alkoxysilane groups (R'''OSi), in manner similar to that described above in conjunction with FIG. 1B. Note that while the modified hemiaminal-type silane material depicted in FIG. 2 includes two Q groups, this is only for purposes of explanation, and the actual product would likely include mixture of materials having from zero to three Q groups attached to the hemiaminal moiety.

As noted, the reaction mixture in FIG. 2 can include at least some additional monomers where x is 2 or 3 (divalent or trivalent Q groups are referred to herein as "linking groups"), but may also include some monomers where x is 1 (monovalent Q groups are referred to herein as "spacer groups"). The Q group may include an aromatic group. These monomers may be an amine-terminated polymer, where Q is a polymeric species.

When Q is a linking group, it may have the general structure:

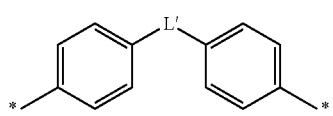

[1]

where L' is a divalent group selected from the group consisting of O, S, N(R'), N(H), R'', and combinations thereof, wherein R' and R'' independently comprise at least 1 carbon, and the starred bond denotes bonding to some other species, which may be a repeating or non-repeating species, not defined in structure [1]. These monomers can have the starred bonds of structure [1] covalently linked to amine nitrogens. Thus, monomers containing structure [1] may have the structure:

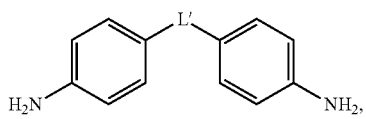

which is the structure Q-(NH$_2$)$_x$ where Q is structure [1] and x is 2.

In the L' group, R' and R'' can represent an organic component independently selected from a group consisting of methyl, ethyl, propyl, isopropyl, phenyl and combinations thereof. Other L' groups in structure [1] include methylene (CH$_2$), isopropylidenyl (C(Me)$_2$), and fluorenylidenyl:

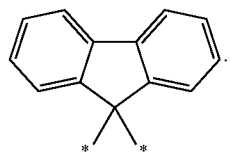

Other examples of divalent linking groups Q include:

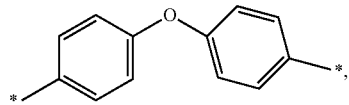

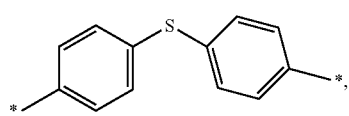

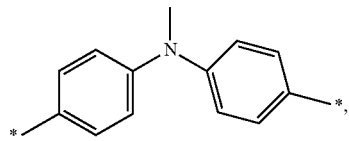

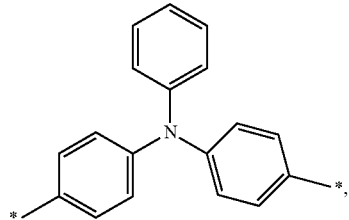

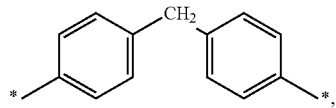

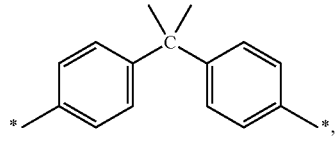

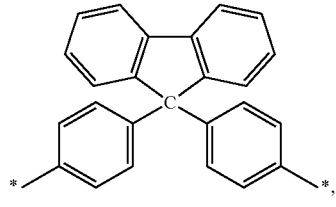

and combinations thereof. The monomers including the above examples of Q groups are diamines including the structures above, where the starred bonds are linked to nitrogen atoms of a primary amine group.

In some examples, Q may be a trivalent linking group. Examples of trivalent linking groups Q include

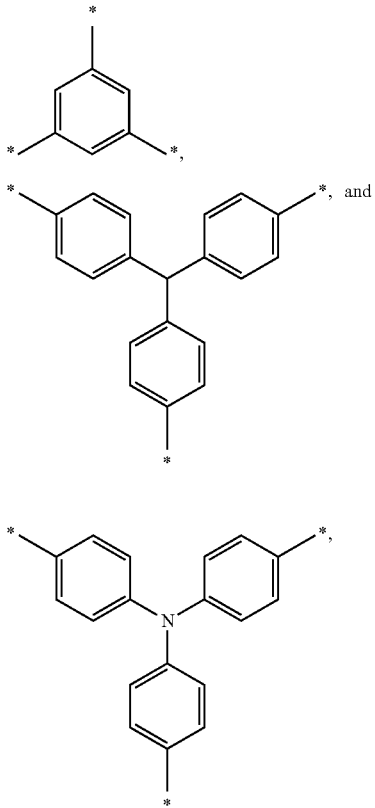

so that the monomers including such groups are triamines where the starred bonds of the above trivalent linking groups are each linked to nitrogen atoms of primary amine groups.

Other monomers which may be incorporated into the reaction mixture also include monoamines Q(NH$_2$), where Q is a spacer group having one of the following structures:

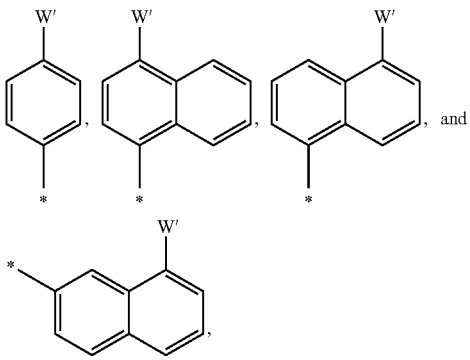

where in each case the starred bond is linked to a nitrogen atom of a primary amine group, W' is a monovalent radical selected from the group consisting of *—N(R$^1$)(R$^2$), *—OR$^3$, —SR$^4$, wherein R$^1$, R$^2$, R$^3$, and R$^4$ are independent monovalent radicals comprising at least 1 carbon. Examples of spacer groups include:

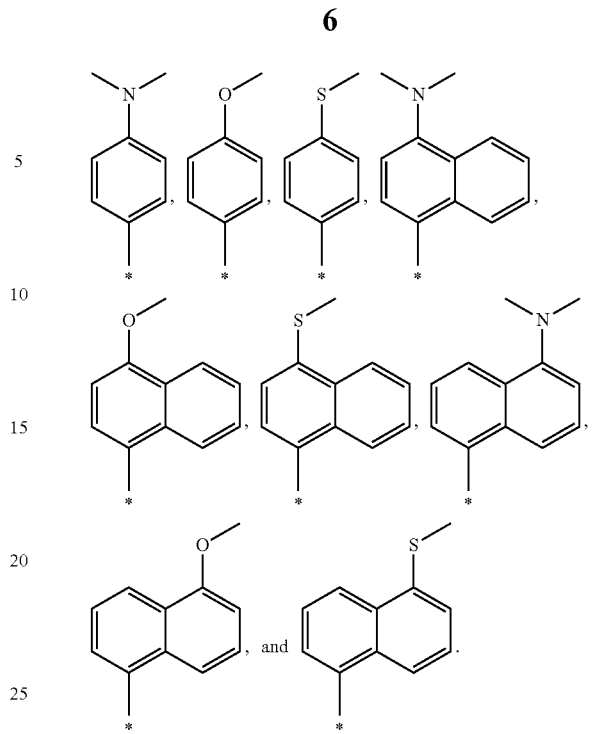

The spacer groups Q can be used in amounts that depend on the characteristics of the desired gel products, and would generally be used in relatively small amounts as compared to the divalent and trivalent monomers.

The divalent and trivalent linking groups may include polymeric or oligomeric groups. For example, the reaction mixture may incorporate a diamine-terminated polymer or oligomer, such as a diamine-terminated vinyl polymer, a diamine-terminated polyether, a diamine-terminated polyester, a diamine-terminated star polymer, a diamine-terminated polyaryl ether sulfone, a diamine-terminated polybenzoxazole polymer, a diamine-terminated polybenimidazole polymer, a diamine-terminated epoxy resin, a diamine-terminated polysiloxane polymer, a diamine-terminated polybutadiene polymer, and a diamine-terminated butadiene copolymer. Diamine-terminated polyethers are commercially available from suppliers such as Huntsman Corp. Diamine-terminated vinyl polymers include long-chain alkyl diamines which may be referred to as polyalkylene diamines, for example polyethylene diamine, polypropylene diamine, and other such polymer diamines. Diamine-terminated vinyl polymers also include long-chain polymer diamines with cyclic and/or aromatic components, such as diamine-terminated polystyrene. The diamine-terminated polymers and oligomers referred to above are commercially available, or may be readily synthesized through well-known reaction pathways.

In some examples, Q may be a polymeric species such as a vinyl polymer chain, a polyether chain, a polyester chain, a polyimide chain, a polyamide chain, a polyurea chain, a polyurethane chain, a polyaryl ether sulfone chain, a polybenzoxazole chain, a polybenimidazole chain, an epoxy resin, a polysiloxane chain, a polybutadiene chain, and butadiene copolymer, or a combination thereof. Typically, a polymer group usable in these methods will have a molecular weight that is at least 1000 g/mole.

In general, polymerization reaction proceeds through the hemiaminal stage at low temperatures (below 80° C.), and at higher temperatures (above 80° C.) water is eliminated as the free amine and hydroxyl groups react to close the ring. The polymer formed at the hemiaminal stage may be referred to as a hemiaminal dynamic covalent network (HDCN). A single polymer chain, network, or mixture may include a mixture of structures depending on how the reaction is performed.

Alkoxysilane Precursor Material

Figure 3:
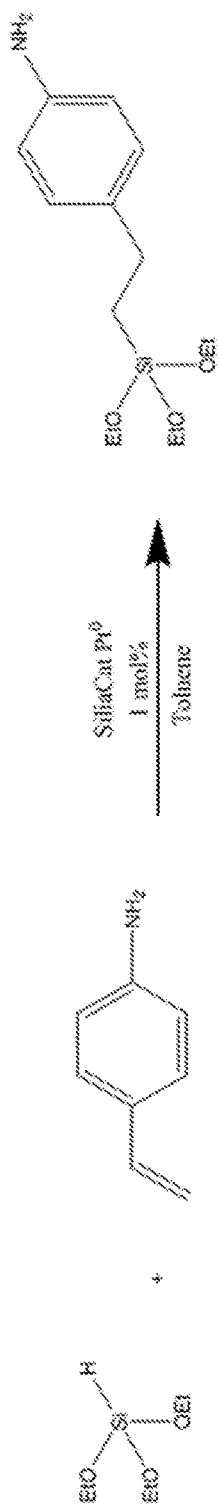
FIG. 3 depicts aspects of a reaction scheme for forming a particular aniline silane material.

FIG. 3 depicts aspects of a reaction scheme for forming a particular aniline silane material. In FIG. 3, triethoxysilane is reacted with 4-aminostyrene in the presence of solid hydrosilylation catalyst ("SiliaCat Pt(0)") comprising sol-gel entrapped platinum nanoparticles encapsulated within a methyl-modified silicate porous matrix to form 4-[2-(triethoxysilyl)ethyl]aniline.

The reaction can be carried under an argon atmosphere at approximately 60° C. for several hours (e.g., 5 to 24 hours) to provide good conversion and selectivity. Details of this reaction can be found in, "Closing the Organosilicon Synthetic Cycle: Efficient Heterogenous Hydrosilylation of Alkenes over SiliaCat Pt(0)," R. Ciriminna et al, *ACS Sustainable Chem. & Eng.*, February 2013, vol. 1, p. 249-253, the contents of which regarding synthesis of organosilicon compounds are incorporated by reference herein.

The scheme in FIG. 3 is merely an example of a reaction that can be used to provide precursor materials for the reactions depicted in FIGS. 1A and 1B. Other alkoxides of silicon incorporating an aryl group functionalized with a primary amine may be obtained by related reactions or by entirely other means.

In some examples, the alkoxysilane precursor material may have the structure:

where R', R", and Q are as defined above.

Example Reaction

Figure 4:
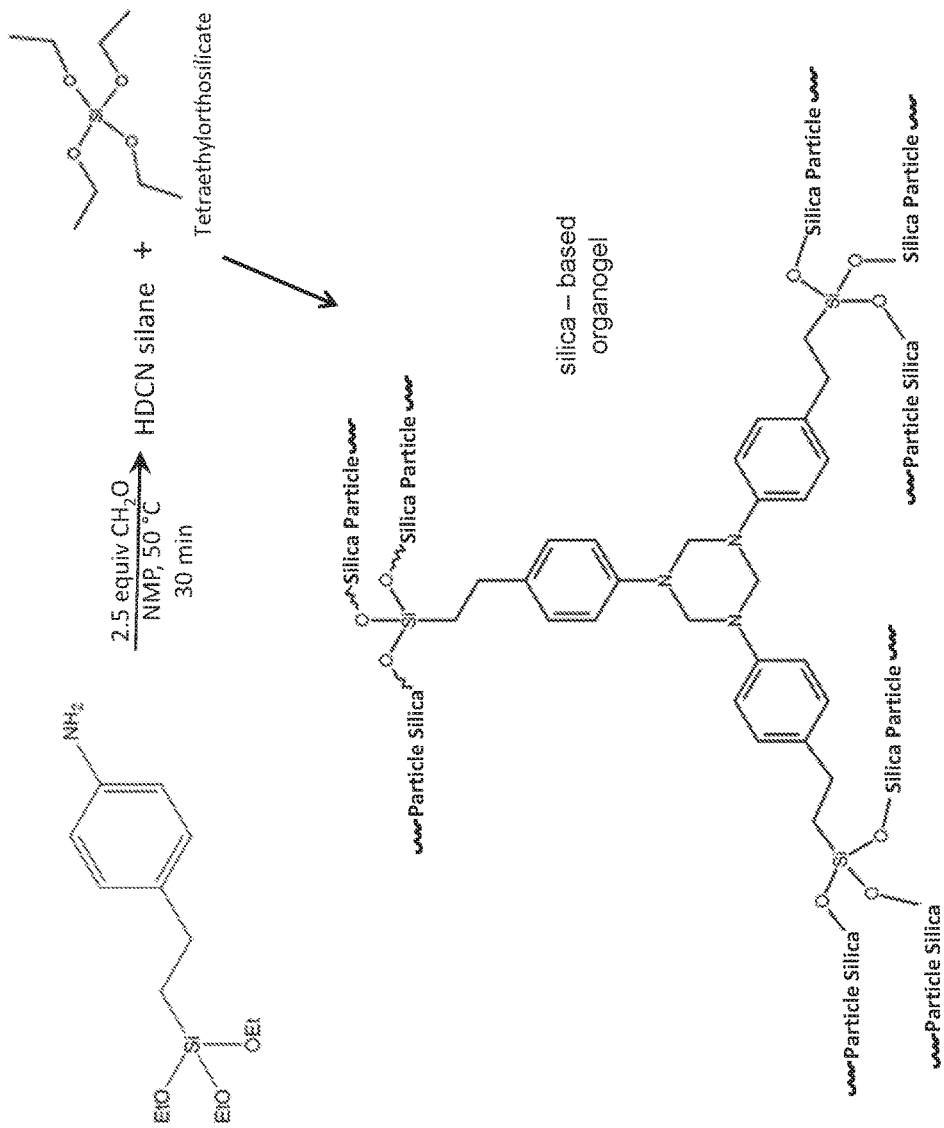
FIG. 4 depicts aspects of a reaction scheme for forming a particular silica-based organogel.

FIG. 4 depicts aspects of a reaction for forming a particular silica-based organogel. In the scheme of FIG. 4, a 4-[2-(triethoxysilyl)ethyl]aniline compound is reacted with 2.5 equivalents of formaldehyde in NMP at 50° C. for 30 minutes. TEOS is subsequently added to the reaction mixture. In some examples, TEOS could be initially present in the reaction mixture instead of subsequently added.

At low temperatures, a hemiaminal-type silane material may be formed (see FIG. 1A) and this material may react with TEOS to form an organo-silica gel incorporating HDCN-type moieties.

At higher temperatures (about 80° C. or higher), or if the organo-silica gel incorporating HDCN-type moieties is heated above about 80° C. or higher, the hemiaminal groups will convert to hexahydrotriazine groups and a silica-based organogel incorporating hexahydrotriazine moieties will be formed.

The number of hemiaminal or hexahydrotriazine groups incorporated into the silica-based organogel will depend on the relative amounts of precursor used in the reaction and the specific reaction conditions adopted.

Method of Preparing Silica-Based Organogels

Figure 5:
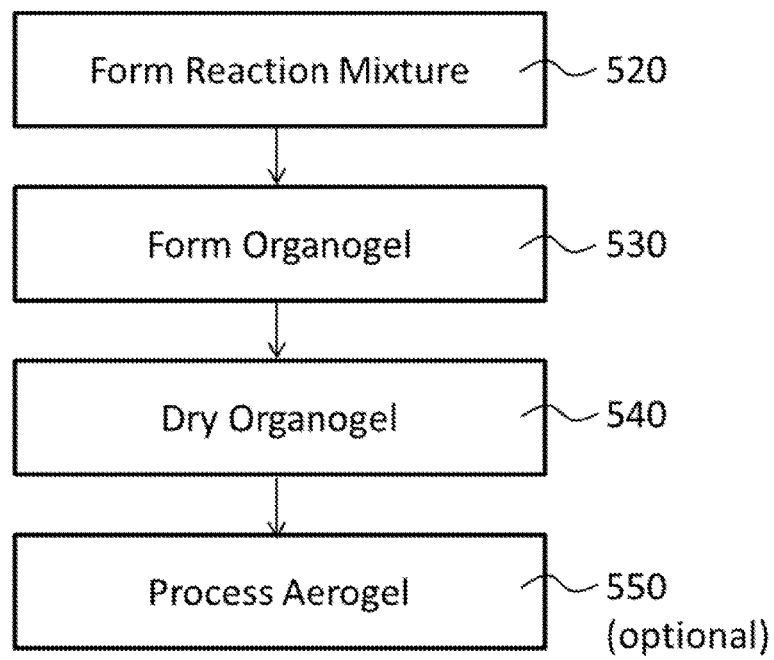
FIG. 5 depicts aspects of a method for forming a silica-based organogel material.

FIG. 5 depicts aspects of a method 500 for forming a silica-based organogel material. In element 520, a reaction mixture is formed. The reaction mixture may include an aniline silane material and formaldehyde to form hemiaminal-type silane material. The reaction mixture may initially include another material, such as TEOS or the like, having alkoxysilane groups, or this other material may be added to the reaction mixture after an initial period. Note, this other material may be optional because the alkoxysilane groups provided by the aniline silane material may be sufficient in some instances to form the silica-based organogel. Likewise, additional monomer(s), such as described in conjunction with FIG. 2, may be included in the reaction mixture. The reaction mixture may include a solvent or solvents. For example, a dipolar aprotic solvent may be included in the reaction mixture.

An organogel results from reaction(s) in the reaction mixture (element 530). This organogel is a polymeric material dispersed in solvent. The properties of the organogel will depend on the reaction conditions, the types and ratios of precursors in the reaction mixture, and type and amount of solvent(s) used in the reaction. In general, the organogel formed in this process preferably has sufficient structural strength to be removed from a reaction vessel and transferred to another vessel, but this is not necessarily required.

In element 540, the organogel is subjected to a drying process to remove the solvent. The gel drying process (solvent removal process) can convert the organogel to an aerogel.

In an example, the solvent removal process can be a supercritical $CO_2$ process. In such a process, the organogel placed in a vessel or chamber in which it can be submerged in a fluid that is a mixture of a drying solvent and liquid $CO_2$. This mixture may be circulated, and the temperature and pressure may be maintained so the mixture remains liquid during this processing. The organogel is allowed to contact the mixture for a time so as to allow the mixture to permeate the gel material and replace the original solvent incorporated into the gel matrix. Drying solvents that may be used with $CO_2$ include alcohols such as methanol and ketones such as acetone. Drying solvents that can be used in this process are preferably low-boiling solvents compatible with the gel matrix and also miscible with the solvent (e.g., NMP) used in the organogel forming reaction. In general, solvents boiling at temperatures less than about 80° C. at atmospheric pressure are suited for this drying process.

The drying solvent-liquid $CO_2$ mixture can be gradually replaced with just liquid $CO_2$. That is, liquid $CO_2$ is flowed into the vessel or chamber containing the gel material, while the drying solvent-liquid $CO_2$ mixture is withdrawn. The overall liquid level in the vessel or chamber may be reduced during this operation to speed removal of higher boiling components.

After flowing liquid $CO_2$ for a suitable time, for example about three residence times of the liquid volume present in the vessel or chamber, temperature can be gradually raised to a point above the critical temperature of the $CO_2$, and then ultimately to room temperature. The vessel or chamber may be sealed during this process, or a flow of $CO_2$ may be continued while the temperature is increased. When conditions exceed the critical point of $CO_2$, the flow of liquid $CO_2$ can be replaced by a flow of supercritical $CO_2$ into the vessel or chamber. When a desired pressure is reached, gas can be vented to maintain the pressure at the desired level. Pressure in the vessel or chamber can be maintained at a pressure above the critical point of $CO_2$, 7.37 MPa, for example between 7.37 MPa and 9.65 MPa. The vapor of the solvent to be removed from the gel may mix with $CO_2$ to form a mixture with critical properties somewhat higher than that of pure $CO_2$. Liquid resulting from extraction of the solvent from the gel can be drained from the vessel.

After exposure to supercritical $CO_2$ is maintained for a time, flow of supercritical $CO_2$ can be stopped, and pressure in the vessel or chamber can be gradually reduced to atmospheric pressure by venting. At this time, a dry aerogel has been formed.

In other embodiments, the gel may be dried (in element 540) by a vacuum process. In such a case, the organogel can be sealed in a vessel or chamber connected to a vacuum source to reduce pressure above the organogel and a flow of a drying gas for removing solvent from the vessel or chamber can be supplied. Maintaining a pressure less than about 500 Torr, for example, provides enhanced solvent removal from the organogel, which would otherwise dry only slowly, or perhaps not at all due to retention of solvent in the spaces between polymer chains of the gel. Heating may also be provided to maintain the gel at a desired temperature as solvent evaporation cools the gel.

The dry aerogel can be removed from the vessel or chamber for additional processing or additional processing may be conducted in the vessel (optional element 550). For example, the dry aerogel can be hardened with an additional heating process and/or may be shaped into layers, sheets, arbitrary shapes, powders, grains, formed into insulating components, incorporated into composite materials, or chemically treated.

The silica-based aerogels formed by the methods described herein generally have improved toughness as compared to typical silica-based aerogels. Silica-based aerogels described herein can also have the ability to be chemically altered and/or recycled after formation. In some cases, a silica-based aerogel incorporating hemiaminal or hexahydrotriazine moieties can be at least partially depolymerized using a warm acid solution, and then remade or reworked from the resulting depolymerized mixture. In other cases, the surface of a resulting silica-based aerogel incorporating hemiaminal or hexahydrotriazine moieties can be functionalized by additional reactions.

Certain chemical structures are presented herein using the following general notation:

[structure]$_n$

This notation is intended to define a repeated chemical structure within a larger structure, or molecule. Use of brackets around a chemical structure, with a letter subscript "n" generally indicates that the structure is repeated "n" times. Letters other than "n" may be used, and in each case, the letter subscript stands for a positive integer of at least 3. Unless otherwise noted, there is no theoretical upper limit to the value of the subscript. The notation is intended to refer to all possible polymers, of any feasible size, having the structure. However, kinetic and thermodynamic circumstances of individual chemical reactions, such as viscosity, temperature, and monomer availability may limit the growth of polymers in specific cases.

The molecular weight of a polymer mixture is usually expressed in terms of a moment of the molecular weight distribution of the polymer mixture, defined as $$M_z = \frac{\sum m_i^z n_i}{\sum m_i^{z-1} n_i},$$

where $m_i$ is the molecular weight of the ith type of polymer molecule in the mixture, and $n_i$ is the number of molecules of the ith type in the mixture, and z is at least 1. $M_1$ is also commonly referred to as $M_n$, the "number average molecular weight". $M_2$ is also commonly referred to as $M_w$, the "weight average molecular weight". The polymer mixtures used to obtain divalent polymer bridging groups in the materials described herein may have $M_1$ of at least about 1000 g/mol.

The molecular weight distribution of a polymer mixture may be indicated by a polydispersity ratio $P_z$, which may be defined as $$P_z = \frac{M_{z+1}}{M_z},$$

where $M_z$ is defined above. The polymer bridging groups used in embodiments described herein typically come from polymer molecule mixtures having a polydispersity ratio $P_1$ of about 1-3, for example about 2.

The chemical structures in this disclosure may denote atomic composition of compounds and relative bonding arrangements of atoms in a chemical compound. Unless specifically stated, the spatial arrangement of atoms depicted in the chemical structures is not intended to be an exact depiction of the spatial arrangement for every embodiment, and those skilled in the chemical arts will recognize that compounds may be similar to, or the same as, the illustrated compounds while having different depicted shapes or conformations. For example, the structures denoted herein may show bonds extending in one direction, while embodiments of the same compound may have the same bond extending in a different direction. Additionally, bond lengths and angles, Van der Waals surfaces, isoelectronic surfaces, and the like may vary among instances of the same chemical compound. Additionally, unless otherwise noted, the disclosed structures cover all stereoisomers of the represented compounds.

While the foregoing is directed to embodiments of the present invention, other and further embodiments of the invention may be devised without departing from the basic scope thereof, and the scope thereof is determined by the claims that follow.

What is claimed is:
1. An aerogel, comprising:
   a plurality of silica groups; and
   a hexahydrotriazine group having at least one nitrogen atom that is covalently linked to at least one silica group in the plurality of silica groups by a linking group.
2. The aerogel of claim 1, wherein the linking group includes an aromatic group.
3. The aerogel of claim 2, wherein the aromatic group is a benzene ring.
4. The aerogel of claim 3, wherein the benzene ring is covalently linked to the at least one silica group via an alkyl group.
5. The aerogel of claim 4, wherein the benzene ring is covalently bonded to a nitrogen atom of the hexahydrotriazing group, and the alkyl group is at a para position of the benzene ring with respect to the covalent bond of the benzene ring to the nitrogen atom of the hexahydrotriazine group.

6. The aerogel of claim 5, wherein the alkyl group is an ethanediyl group.

7. The aerogel of claim 4, wherein the alkyl group is an ethanediyl group.

8. The aerogel of claim 1, wherein each nitrogen atom of the hexahydrotriazine group is covalently linked to at least one silica group in the plurality of silica groups.

9. The aerogel of claim 1, wherein the silica groups are nanoparticles of silica.

10. The aerogel of claim 1, wherein the linking group has the structure:

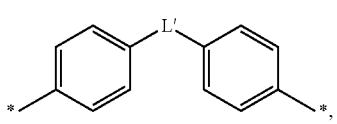

wherein a nitrogen atom of the hexahydrotriazine group is covalently linked at one starred bond of the linking group, L' is a divalent group selected from the group consisting of O, S, N(R'), N(H), and R", wherein R' and R" each comprise at least 1 carbon, and the other starred bond of the linking group is bonded to a nitrogen atom of another hexahydrotriazine group.

11. An insulating material, comprising:
   an organo-silica gel including:
      a plurality of silica groups; and
      a hexahydrotriazine group having at least one nitrogen atom of the hexahydrotriazine group covalently linked to at least one silica group in the plurality of silica groups.

12. The insulating material of claim 11, wherein the organo-silica gel is an aerogel.

13. The insulating material of claim 11, wherein the at least one nitrogen atom of the hexahydrotriazine group is covalently linked to the at least one silica group via an aromatic group and an alkyl group.

14. The insulating material of claim 11, wherein the hexahydrotriazine group has the following structure:

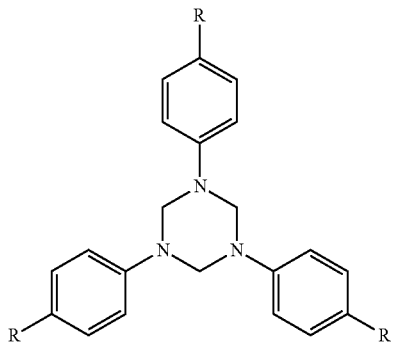

wherein each R group independently represents an alkanediyl group covalently linked to at least one silica group in the plurality of silica groups.

15. The insulating material of claim 11, wherein a nitrogen atom of the hexahydrotriazine group is covalently linked, at one starred bond, to a linking group having the structure:

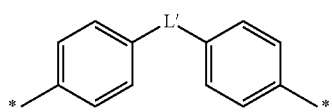

wherein L' is a divalent group selected from the group consisting of O, S, N(R'), N(H), and R", wherein R' and R" each comprise at least 1 carbon, and the other starred bond of the linking group is bonded to a nitrogen atom of another hexahydrotriazine group.

* * * * *